(12) United States Patent
Miller et al.

(10) Patent No.: US 7,048,379 B2
(45) Date of Patent: May 23, 2006

(54) IMAGING LENS AND ILLUMINATION SYSTEM

(75) Inventors: Joseph Marion Miller, Tucson, AZ (US); James Theodore Schwiegerling, Oro Valley, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 10/801,573

(22) Filed: Mar. 17, 2004

(65) Prior Publication Data

US 2005/0041207 A1 Feb. 24, 2005

Related U.S. Application Data

(60) Provisional application No. 60/455,297, filed on Mar. 17, 2003.

(51) Int. Cl.
*A61B 3/10* (2006.01)
*A61B 3/00* (2006.01)
*A61B 3/14* (2006.01)

(52) U.S. Cl. .................. 351/213; 351/205; 351/207; 351/221; 351/246; 600/473; 600/476

(58) Field of Classification Search ................ 351/200, 351/205, 206, 207, 208, 211, 212, 213, 214, 351/221, 222, 246
See application file for complete search history.

(56) References Cited

U.S. PATENT DOCUMENTS

| | | | | | |
|---|---|---|---|---|---|
| 3,700,858 | A | * | 10/1972 | Murthy | 235/462.25 |
| 3,850,527 | A | * | 11/1974 | Winthrop et al. | 356/129 |
| 4,247,176 | A | * | 1/1981 | Ito | 351/207 |
| 4,660,945 | A | * | 4/1987 | Trachtman | 351/203 |
| 4,859,051 | A | * | 8/1989 | Fukuma et al. | 351/211 |
| 5,752,767 | A | * | 5/1998 | Muehlemann | 362/277 |
| 2005/0018136 | A1 | * | 1/2005 | Hayashi | 351/212 |

* cited by examiner

*Primary Examiner*—Eric F. Winakur
*Assistant Examiner*—John R Sanders
(74) *Attorney, Agent, or Firm*—Oblon, Spivak, McClelland, Maier & Neustadt, P.C.

(57) ABSTRACT

An imaging system and method for imaging an object, where an objective lens directs light to the object, a coupling lens receives light reflected from a surface of the object and transmitted through the objective lens, and focuses the reflected light as an image of the object, and an annular light emitter arranged concentrically with an optical axis of the objective lens and the coupling lens emits to the objective lens the light directed to the object.

75 Claims, 14 Drawing Sheets

IMAGING LENS AND ILLUMINATION SYSTEM

CROSS REFERENCE TO RELATED APPLICATIONS

This application is related to U.S. Provisional Application Ser. No. 60/455,297, filed on Mar. 17, 2003, entitled "A Fundus Imaging Lens and Illumination System," the entire contents of which are incorporated herein by reference.

BACKGROUND OF THE INVENTION

1. Field of the Invention

This invention relates to the field of optical imaging to which it has general application and particularly is related to optometry and the diagnostic equipment used therein, and more specifically ophthalmic imaging equipment and methods for examining the eye and other suitable parts of the body.

2. Description of the Related Art

Visualizing or photographing interior structures of the human eye (i.e., the ocular fundus) is difficult because the entrance pupil of the eye is limited to a diameter of around 10 mm. Through this image area, both illumination pathways and imaging pathways must co-exist but not create glare. Traditional mechanisms to accomplish this function are to provide separate areas of the pupil for an illumination point source, as well as an aerial image of the entrance pupil of the camera through this shared human pupil. Further, interior eye structures must be imaged through the cornea, which inserts in the optical path a highly reflective surface. Thus, through this image area, both illumination pathways and imaging pathways must co-exist and not create glare or undesirable reflections.

A conventional fundus camera as shown in FIG. 1A includes a light source 2 and an optical arrangement for directing light from the light source through the cornea and pupil to the internal eye structure to be imaged. The light from the light source is focused into the eye by an objective lens 4. Light reflected from the eye (e.g., from the retina) travels out of the eye and enters the coupling (i.e., the fundus camera imaging) lens 6, which focuses the image to be captured on an image recorder 8 (i.e., a film or a digital sensor). The light source 2 can be an illumination bulb and/or an electronic flash directed toward the eye by a complex arrangement of optical components that include beam splitters, mirrors, and condensing lenses. As shown in FIG. 1A, in one conventional approach, light from the bulb or flash is reflected from an annular light reflector 10 to form an annulus of light, which is projected into the eye. Light reflected from the eye structure of interest passes out of the eye and through the center of the annular light reflector 10, and back to the image recorder 8. This approach minimizes undesirable reflections by insuring that illumination and reflected light pass through separate regions of the pupil and do not overlap on passing through the cornea. Furthermore, undesirable back reflections from the cornea are minimized in conventional fundus imaging systems by using a black dot in the center of the objective lens 4 to minimize undesirable reflection from the cornea along the central optical axis.

Such fundus cameras in either handheld, mounted, or desktop configurations must accommodate the light source and the associated beam forming and imaging optical elements described above for illumination and imaging, making conventional fundus imaging systems large, heavy, complex, and expensive. While simpler systems for imaging the retina exist, the illumination scheme as shown in FIG. 1B typically use a prism or beam splitter 12 to direct light from the light source 4 into the eye. This approach while simpler than that shown in FIG. 1A suffers due to inadvertent light scattering in the eye. For example, as shown in FIG. 1B, the illumination in this approach enters the eye pupil eccentrically, so the reflection from the cornea does not reflect back into the device, but instead reflects at some angle away from the entrance pupil of the imaging system. Further, the amount of illumination that can be directed into the eye is limited in this approach, and the illumination and imaging pathways overlap. Scattering occurs within the cornea and crystalline lens and obscures the image of the internal structure of the eye.

SUMMARY OF THE INVENTION

One object of the present invention is to permit application of high-resolution digital imaging systems (which are very light sensitive) for recording details of the interior structure of objects such as for example the human eye or other organs and joints and also non-anatomical objects.

Indeed, another object of the present invention is to provide an imaging system in which the imaging system illuminates the object with an annular light source.

Still another object of the present invention is to provide an imaging system in which the imaging system illuminates the object without transmitting light from the light source through a central region of an objective lens in front of the object.

Another object of the present invention is to provide a fundus imaging system which is less complex and bulky compared to the traditional fundus imaging systems Still another object of the present invention is to provide a fundus imaging system in which the imaging system images an indirectly illuminated portion of the eye such as the ocular fundus by illuminating directly other portions such as the crystalline lens and cornea.

Correspondingly, one problem with incorporating illumination and imaging in the same optics is back reflections from surfaces. Back reflections typically cause an out-of-focus spot to be formed over the top of recorded image. The advantage for using the same optics is a compact imaging system. Thus, the present invention presents configurations that eliminate back reflections, but keep imaging and illumination properties acceptable.

According to one aspect of the present imaging system, there is provided a baffle to prevent light from the annular light emitter from striking center of objective lens and back reflecting into image recorder. The objective lens forms an intermediate image of retina and the coupling lens couples this intermediate image into the digital camera optics.

Various of these advantages and other objects are provided for in the various embodiments of the present invention.

In one embodiment of the present invention, a novel imaging system is provided for imaging an object. The system includes an objective lens configured to direct light to the object. The system includes a coupling lens configured to receive light reflected from a surface of the object and transmitted through the objective lens, and to focus the reflected light as an image of the object. The system includes an annular light emitter arranged concentrically with an optical axis of the objective lens and the coupling lens, the annular light emitter being configured to emit to the objective lens the light directed to the object.

In one embodiment of the present invention, a novel imaging system is provided for imaging an object. The system includes a light source configured to emit light for illumination of the object, includes an objective lens configured to direct the light to the object, includes a coupling lens configured to receive light reflected from a surface of the object and transmitted through the objective lens, and to focus the received light as an image of the object, and includes a baffle inserted in an optical path from the light source and the objective lens. The baffle is configured to block light from the light source from being incident on a central region of the objective lens.

In another embodiment of the present invention, a novel imaging system is provided for imaging an object. The system includes a light source configured to emit light for illumination of the object, includes an objective lens configured to direct the light to the object, and includes a coupling lens configured to receive light reflected from a surface of the object and transmitted through the objective lens, and to focus the received light as an image of the object. The light source includes an infrared light source configured to irradiate the object with infrared light for alignment of the object prior to image capture.

In still another embodiment of the present invention, a novel imaging system is provided for imaging an object. The system includes a light source configured to emit light for illumination of the object, includes an objective lens configured to direct the light to the object, and includes a coupling lens configured to receive light reflected from a surface of the object and transmitted through the objective lens, and to focus the received light as an image of the object. The light source includes a white light emitting diode and a green light emitting diode.

In another embodiment of the present invention, a novel method images an object by emitting light from an annular light emitter arranged concentrically with an optical axis for illuminating the object, directing the light to the object; receiving and focusing reflected light from a surface of the object, and forming an image of the object.

In another embodiment of the present invention, a novel computer readable medium contains program instructions for execution on a computer system. The program instructions, when executed by the computer system, cause the computer system to image an object by controlling light emission from an annular light emitter arranged concentrically with an optical axis for illuminating the object, and capturing the image of the object from light directed to the object from the annular light emitter, reflected from a surface of the object, and imaged onto an image recorder.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 2:
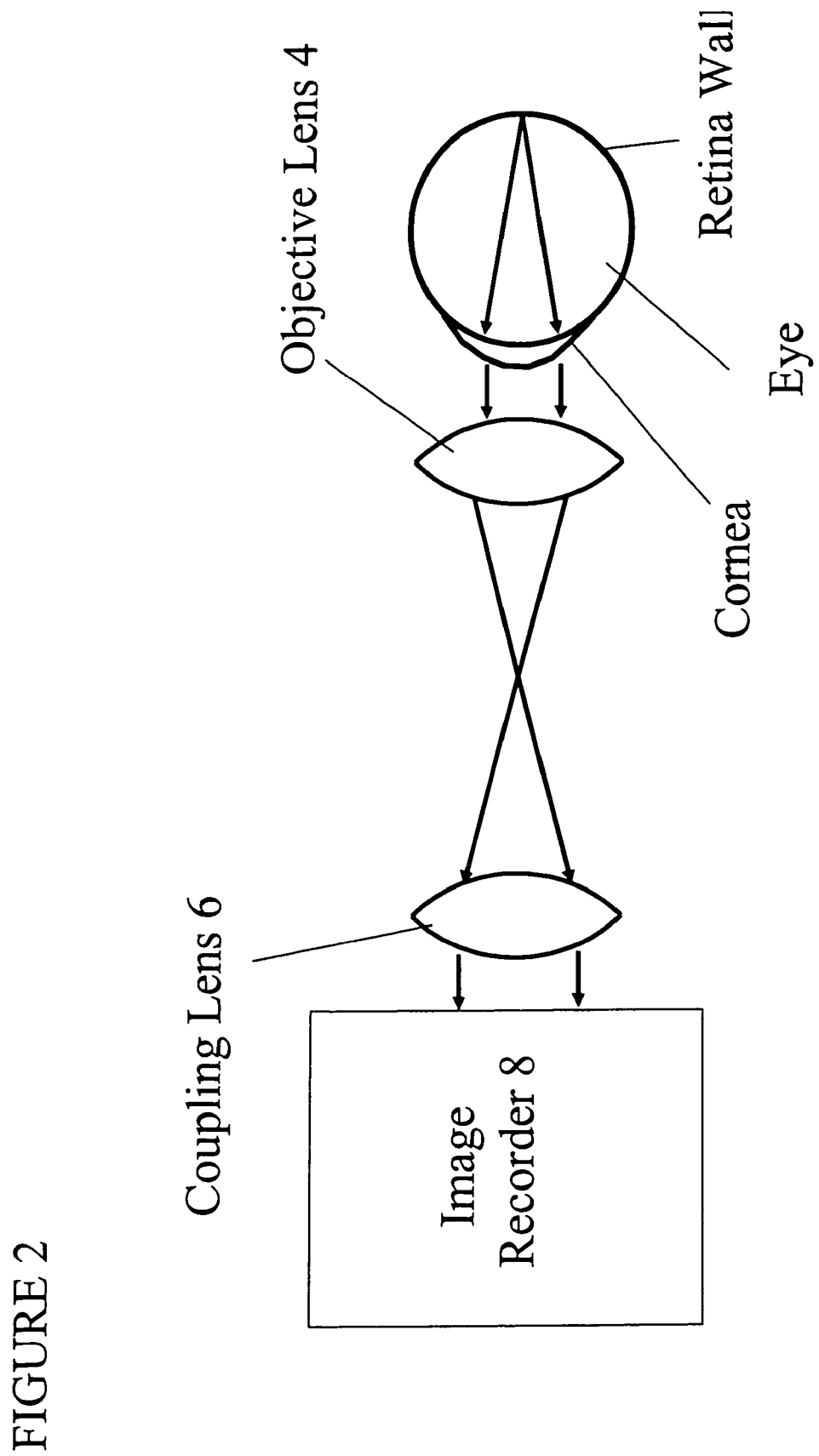
FIG. 2 is a schematic illustrating imaging the interior structure of an eye with an objective lens.

Referring now to the drawings, wherein like reference numerals designate like or corresponding parts throughout the several views, and more particularly to FIG. 2, FIG. 2 illustrates problems in illuminating the interior structure of an eye, especially a human eye. As shown in FIG. 2, light reflecting from the retinal surface must pass through the cornea and the fundus lens and pupil behind the cornea before then passing through the objective lens 4 and coupling lens 6 to the image recorder 8. While coatings such as anti-reflective coatings can be added to the external lens (i.e. the objective lens 4 and coupling lens 6) to minimize image transmission losses, the complexities of the reflections and transmissivity of the cornea, pupil, and fundus lens are beyond control of the eye examiner.

Figure 3:
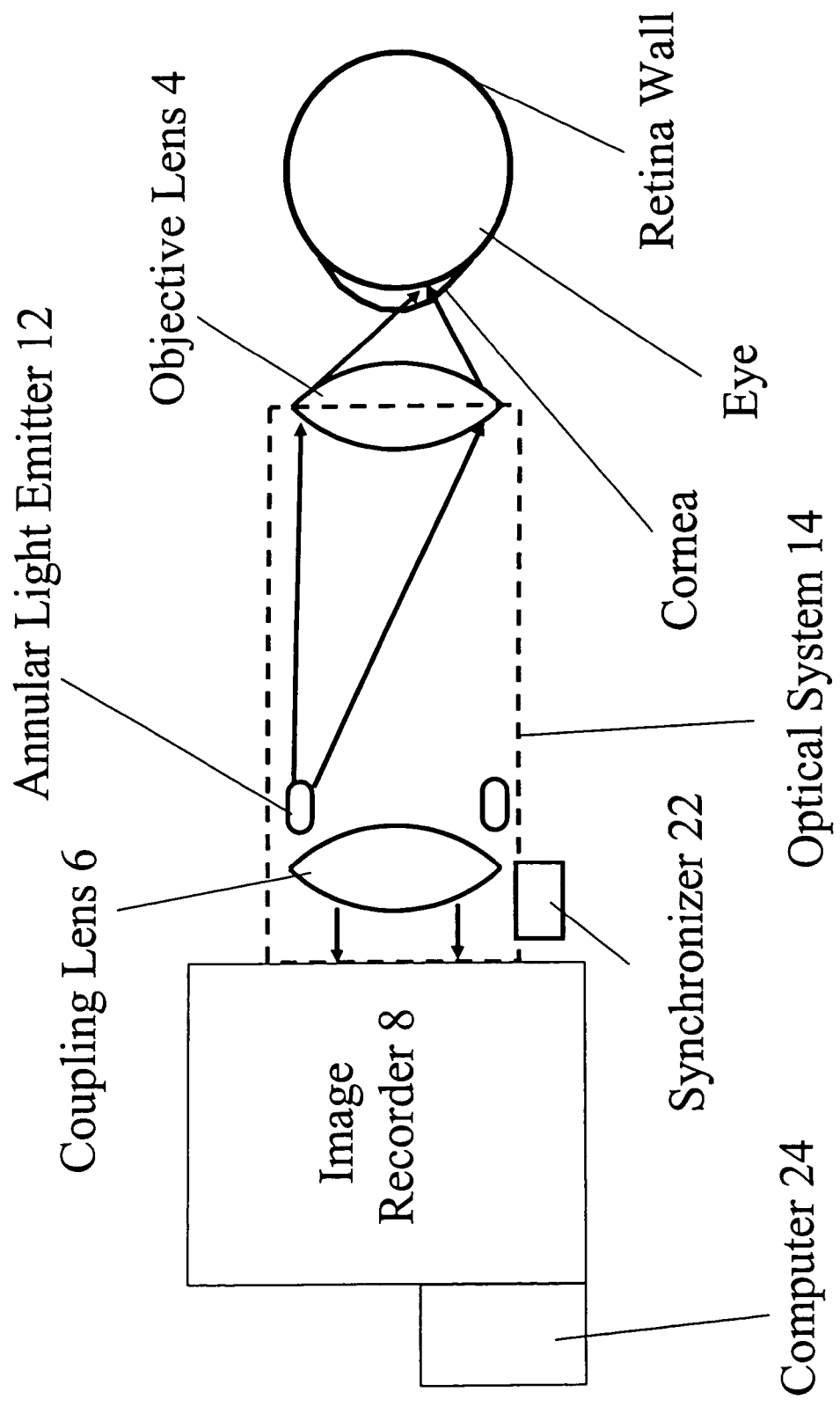
FIG. 3 is a schematic ray diagram for illuminating the interior of the human eye.

FIG. 3 illustrates one approach of the present invention used to reduce glare by indirectly illuminating portions of the eye such as for example the ocular fundus by illuminating directly other portions such as the crystalline lens and cornea from an annular light emitter 12. In one preferred embodiment of the present invention, any reduction in image intensity caused by the indirect illumination is compensated for by the sensitivity of the image recorder 8, such as for example a Nikon Cool Pix 950 megapixel camera. While such digital cameras are preferred, the present invention is not limited to high-sensitivity digital cameras such as the one noted above. Other suitable digital cameras and other image recorders such as film-based recorders and even the eye of the eye examiner can be used with the optical system 14 of the present invention. Regardless, the image recorder 8 captures images of the interior structures of the human eye for subsequent medical analysis.

Figure 1A:
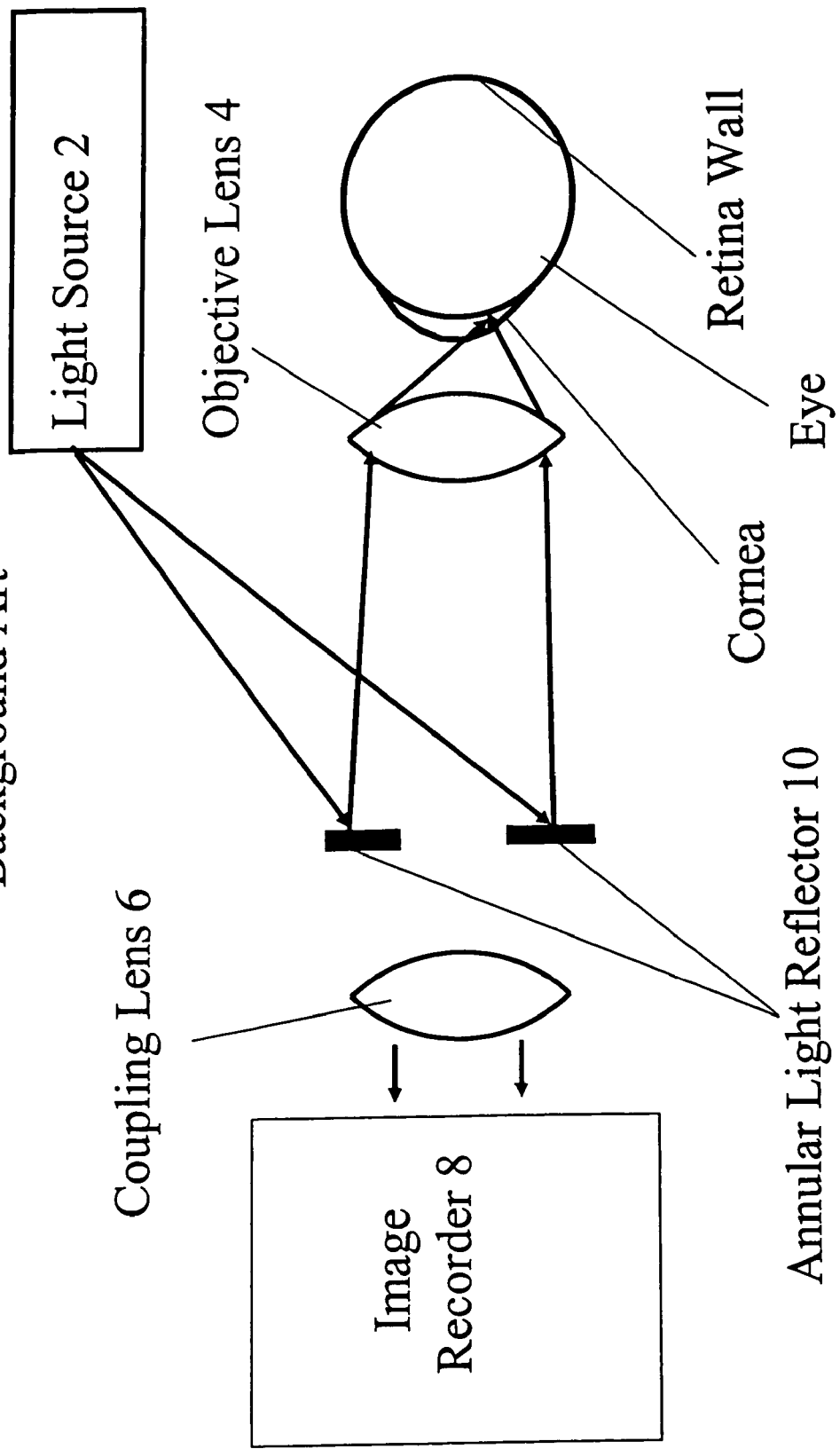
FIG. 1A is a schematic of a conventional ophthalmic imaging system.
Figure 1B:
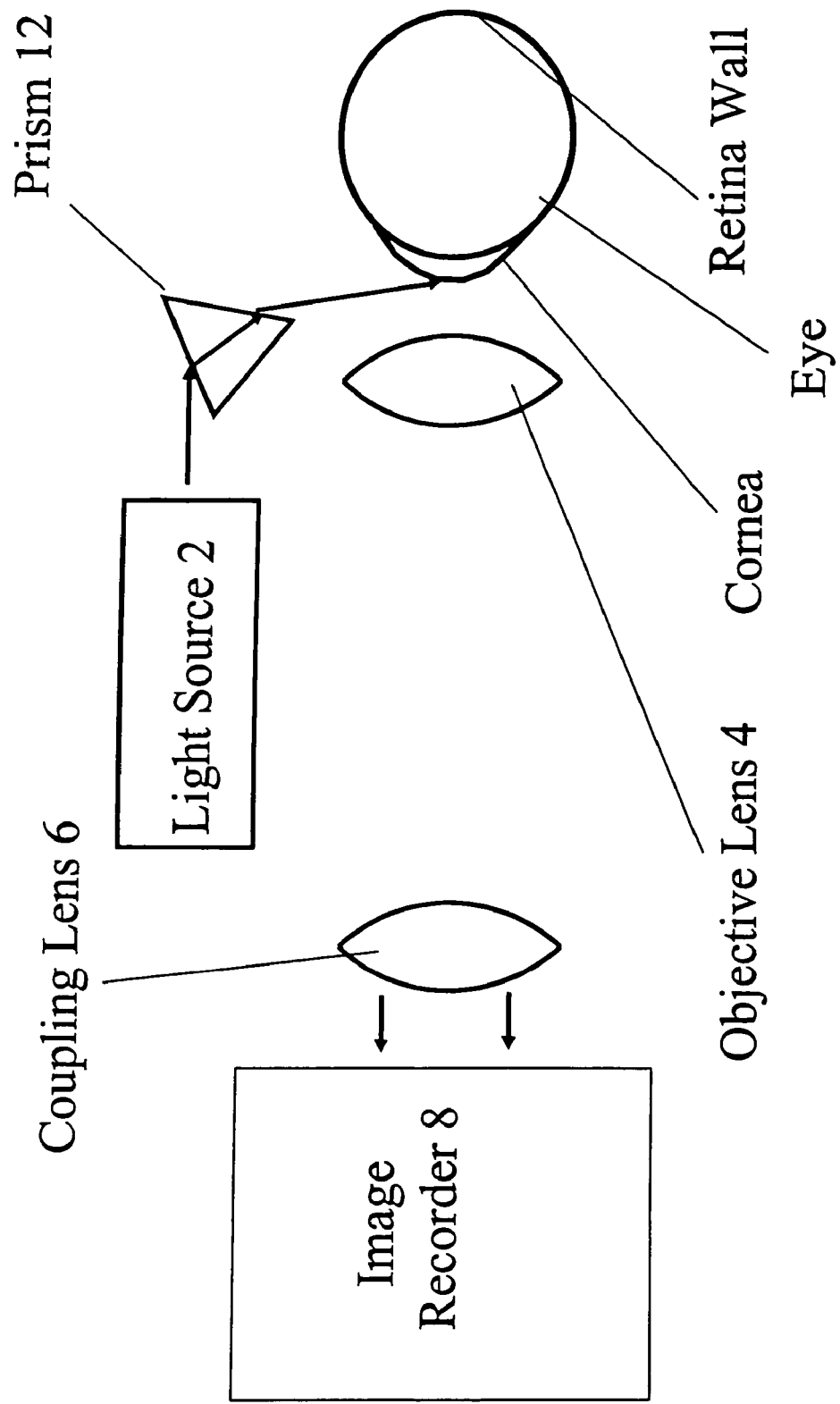
FIG. 1B is a schematic of another conventional ophthalmic imaging system.
Figure 4:
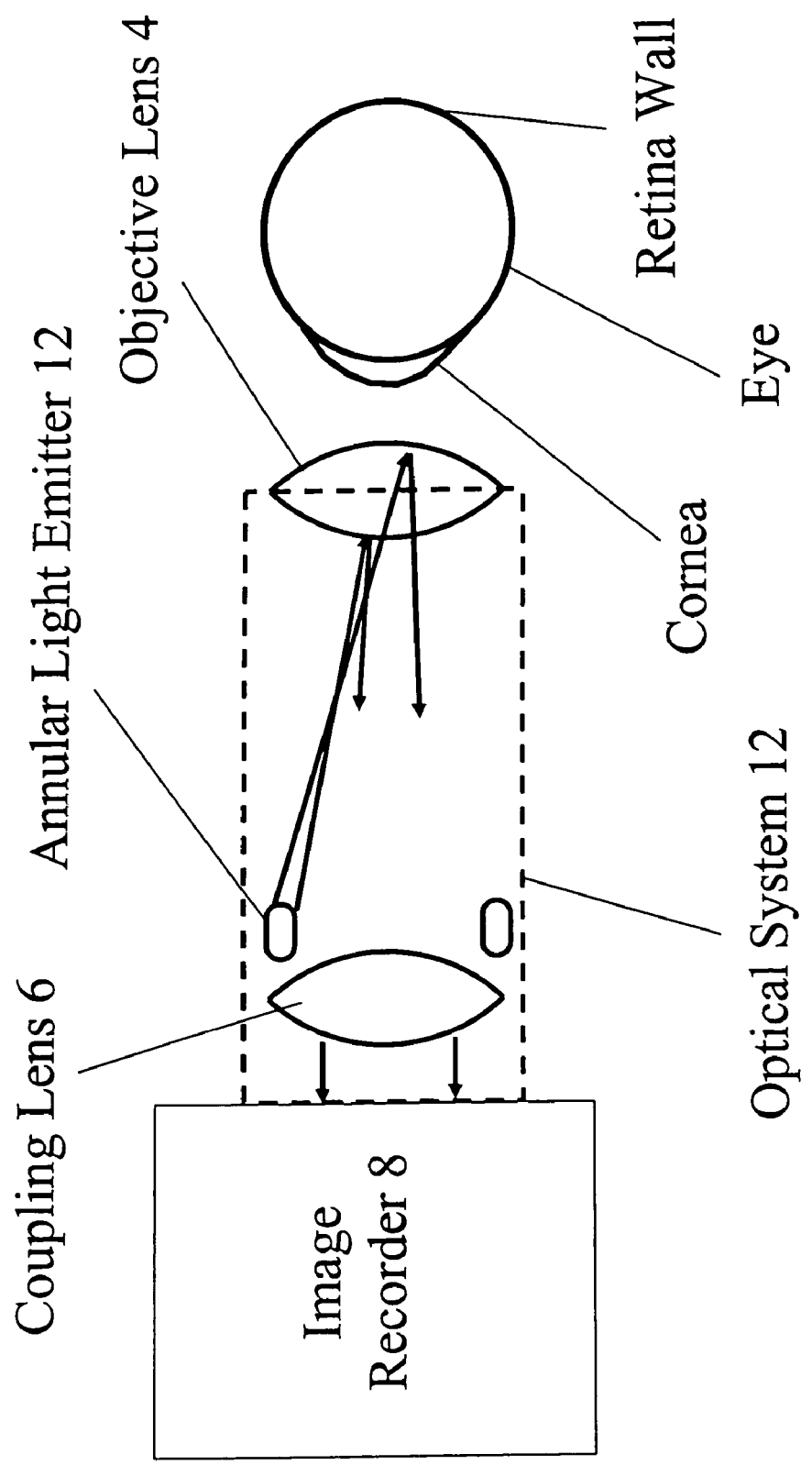
FIG. 4 is a schematic diagram illustrating inadvertent reflection of light from an annular light source off a first surface of the objective lens back into an image recorder.
Figure 5:
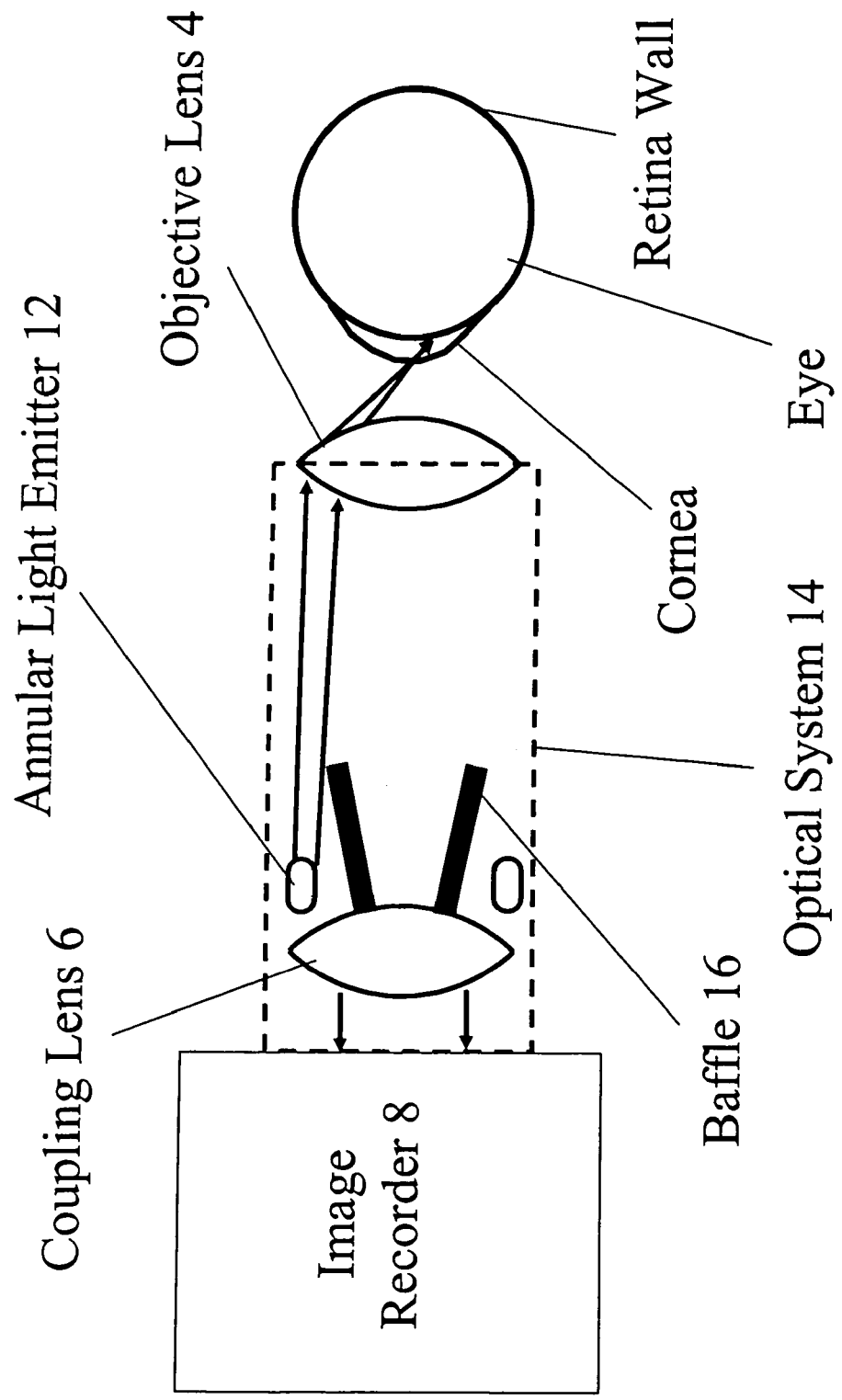
FIG. 5 is a schematic diagram of the novel imaging system of the present invention illustrating a preferred embodiment utilizing a first baffle to illuminate light from being in inadvertently reflected from the objective lens into an imager recorder such as for example a digital camera.

FIG. 4 is a schematic diagram illustrating inadvertent reflection of light from an annular light emitter 12 (or from example the annular light reflector 10 illustrated in FIG. 1) off a first surface of the objective lens back into the image recorder. Such light provides "glare" in the recorded image deteriorating the quality. Accordingly, in a preferred embodiment of the present invention, a baffle 14 is provided between the annular light emitter 12 and the objective lens 4, as shown in FIG. 5. The baffle 16 included in the optical system 14 prevents back reflections from the surfaces of the objective lens 4 from being detected by the image recorder 8. As shown in FIG. 4, the baffle 16 being made of an opaque material is configured to subtend an angle that prevents light from the annular light emitter 12 from being transmitted to a central region of the objective lens 4. Ideally, the baffle 16 is a hollow conical frustrum with its small end sufficiently large to encompass the entrance pupil of the coupling lens/image recorder combination and small enough to fit within the annular light emitter 12. The large end of the conical frustum is sufficiently large to accommodate the image recorder's field of view, but no so large that light from the annular light emitter 12 cannot reach the objective lens 4. Ideally, the baffle 16 has an angular subtense corresponding to the field of view of the image recorder. A wider angular subtense blocks light from the annular light source unnecessarily and a narrower baffle will clip the corners of the image recorder by the image recorder 8. The baffle 16 can be made of any suitable opaque material.

Due to the radius of curvature of the objective lens 4 at the points where light from the annular light emitter 12 arrives at the objective lens 4, light at those points is reflected away from the image recorder 8. Thus, the parameters of the baffle 16 will depend upon the surface shapes and index of refraction of the objective lens 4. In theory, without the baffle 16 of the present invention, there will exist a ray of light leaving the annular light emitter 12 that reflects from the surface of the objective lens 4 and passes back to the image recorder 8. With the baffle 8, this light ray is obscured.

Figure 6:
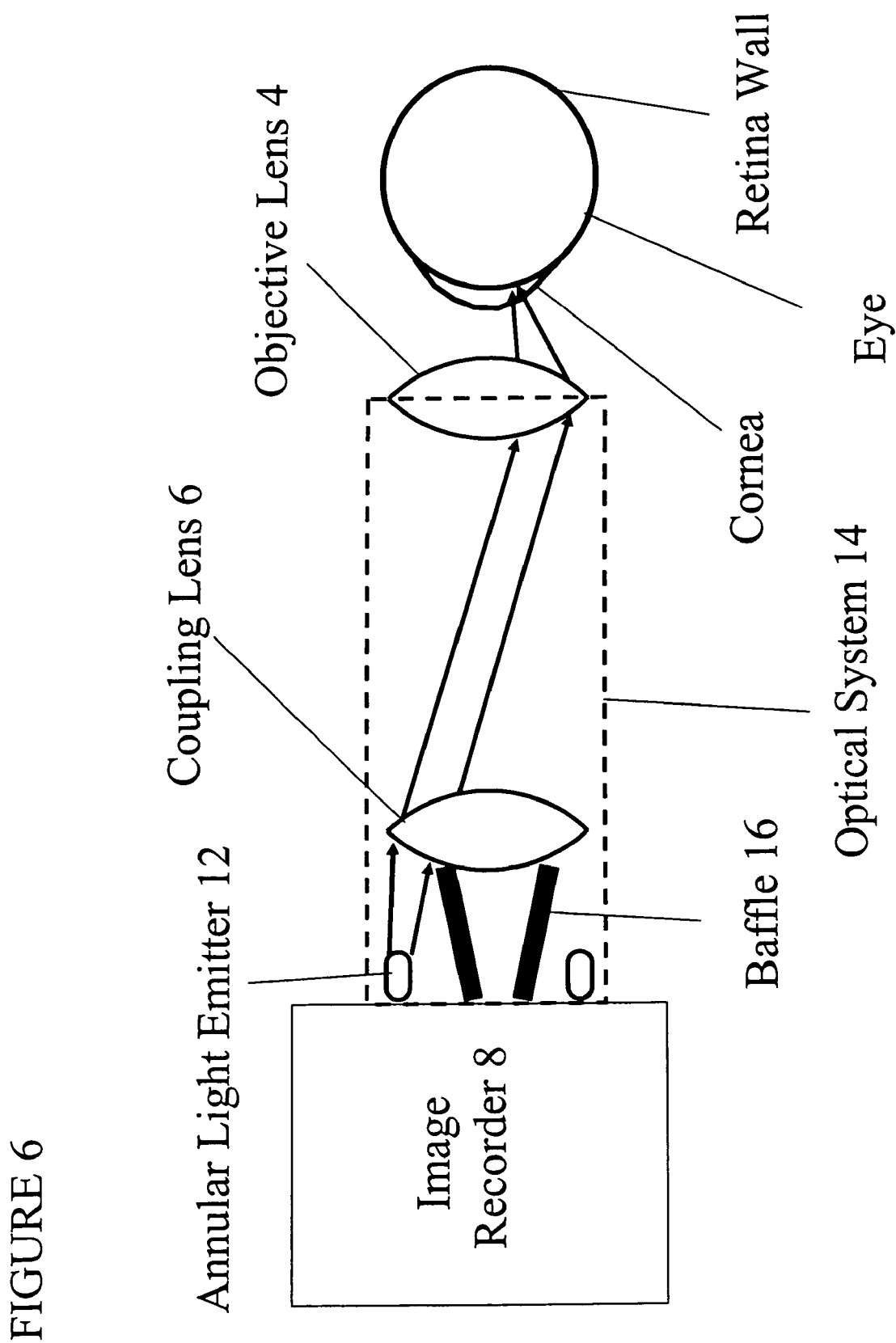
FIG. 6 is a schematic diagram of the novel imaging system of the present invention illustrating another preferred embodiment utilizing a second baffle to illuminate light from being in inadvertently reflected from the objective lens into the image recorder.

FIG. 6 is a schematic diagram of the novel imaging system of the present invention illustrating a second baffle configuration in the optical system 14 of the present invention. As shown in FIG. 6, to illuminate light from being in inadvertently reflected from the objective lens 4 into the image recorder 8, the annular light emitter 12 is positioned between the image recorder 8 and the coupling lens 6, and a baffle 16 similar to the first described baffle configuration is disposed between the annular light emitter 12 and the coupling lens 6. The baffle 16 in the second configuration again prevents back reflections from the surfaces of the objective lens 4 from being detected by the image recorder 8.

Figure 7:
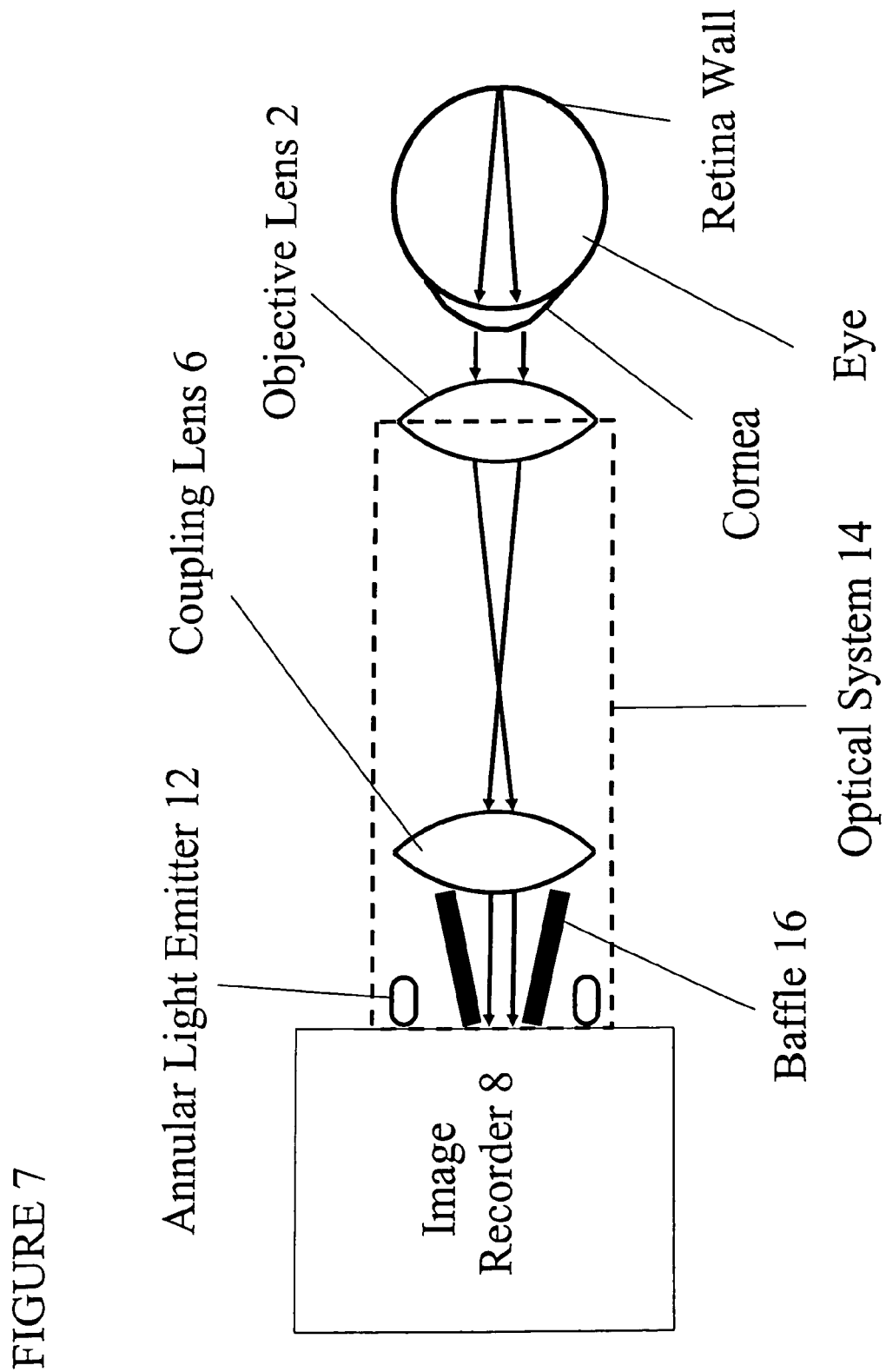
FIG. 7 is a schematic diagram of the novel imaging system of the present invention illustrating imaging occurring while using the second baffle of the present invention.

FIG. 7 is a schematic diagram of the novel imaging system of the present invention illustrating imaging occurring while using the baffle 16 of the present invention in still a third configuration. The baffle 16 again prevents back reflections from the surfaces of the objective lens 4 from being detected by the image recorder 8.

The following is an exemplary list of components suitable for an imaging system of the present invention including the optical system 14. The imaging system of the present invention includes the annular light emitter 12 preferably a white-light emitter, the objective lens 4, the image recorder 8, preferably a lens mount included in the optical system 14 which allows reliable and rigid attachment of lenses 4 and 6 and the annular light emitter 12 to the image recorder 8, and a coupling lens 6 that allows the image to be focused at optical infinity and provides for magnification of the fundus image, and preferably a light baffle 16.

Figure 8A:
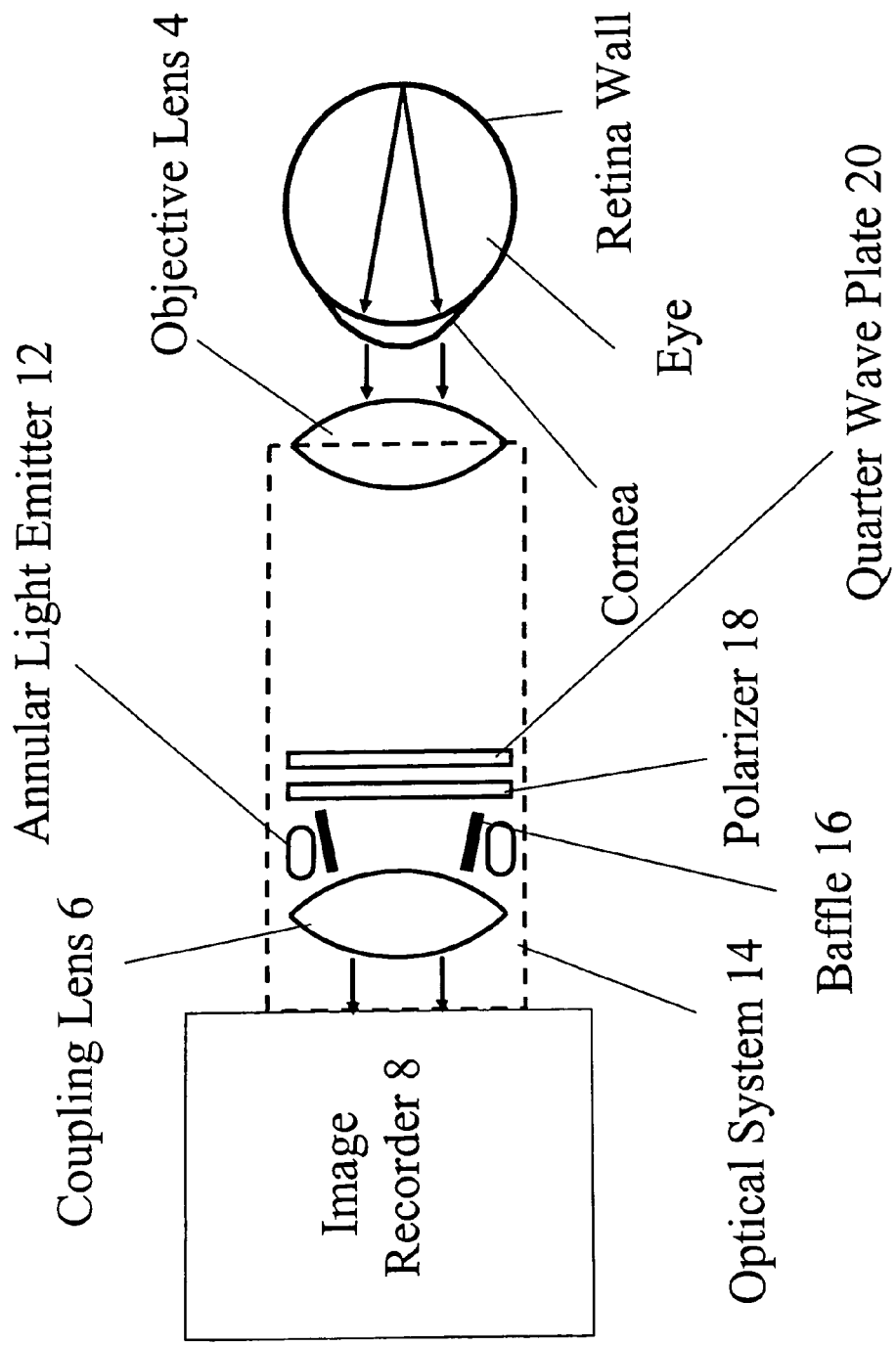
FIG. 8 is a schematic diagram of the novel imaging system of the present invention including a linear polarizer and a quarter wave plate.

Further, in one embodiment of the present invention as shown in FIG. 8A, preferably a linear polarizing filter 18 and a quarter-wave circular polarizing plate 20 are included to minimize inadvertent reflections from the front and back surface of the objective lens 4 from being recorded by the image recorder 8.

Figure 8B:
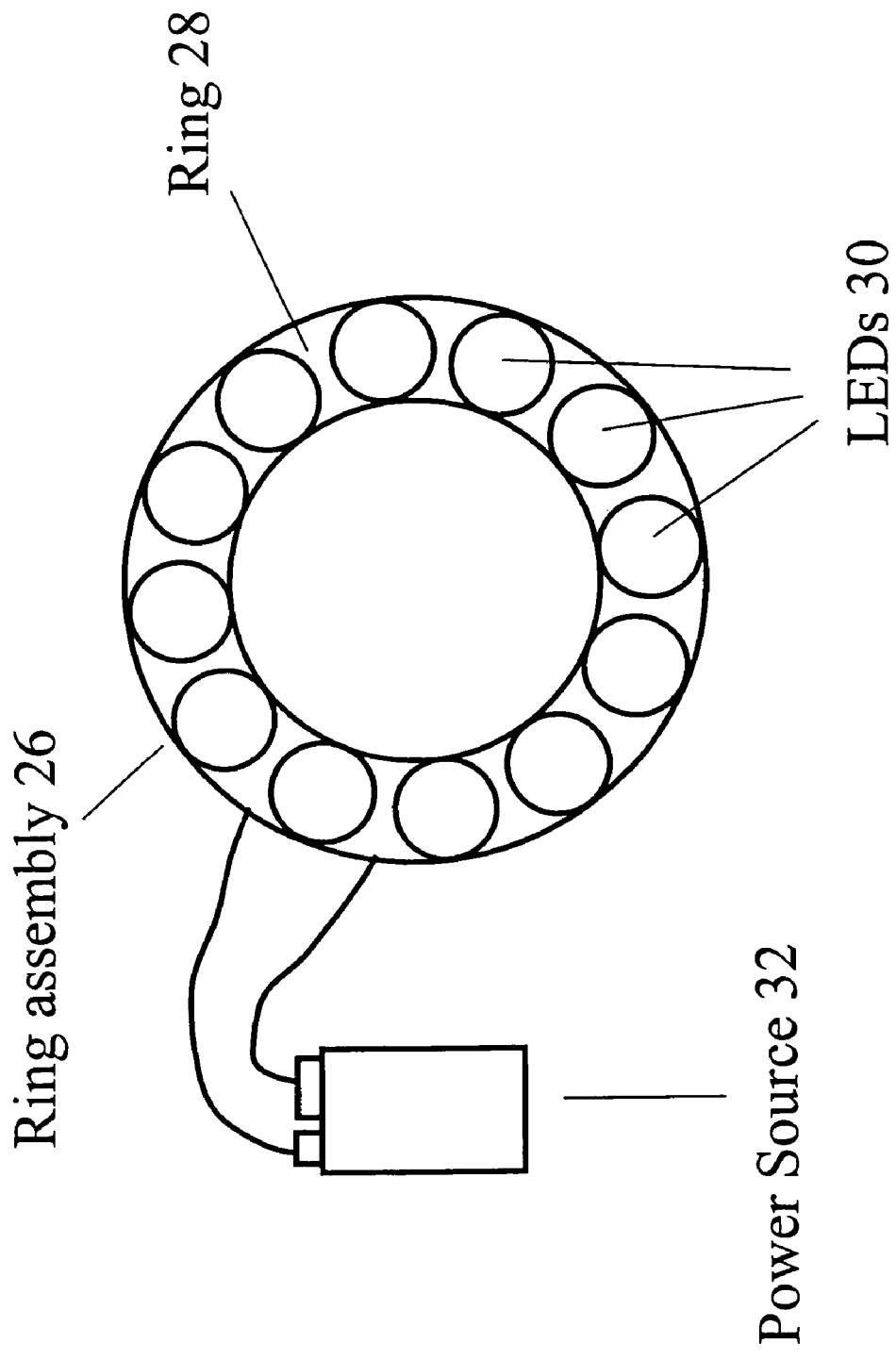

The coupling lens 6 has a refractive power in a range from 5 to 60 diopters, and is preferably a 10-diopter (100 mm) focal length lens. The diameter of the coupling lens 6 prevents retro-illumination from the annular light emitter 12. Light leaking from the sides and back of LEDs of the annular light emitter 12 should not be able to go through the coupling lens 6 and enter into the imaging recorder 8. This is accomplished by the diameter of the coupling lens 6 and the mounts (not shown) that hold the coupling lens 6 in place. The annular light emitter 12 is preferably a ring assembly 26 as shown in FIG. 8B. The ring assembly 26 can include for example a ring 28 of light-emitting diodes 30 using for example white-light North American Optic LED emitters (Jameco part #142885), that are of the type T1 size and which produce approximately 600 millicandela white light at 20 milliamperes each. The ring assembly 26 in one preferred embodiment of the present invention is constructed by a circuit board assembly, and is constructed so that the light-emitting diodes 30 fall along an axis toward the center of the human eye's pupil. As shown in FIG. 8B, a power source 32 such as for example a battery can power the light-emitting diodes 30.

The objective lens 4 is preferably a one piece aspheric lens. A typical range of powers for the objective lens 4 is 20 to 90 diopters depending on the desired field of view and magnification of the structures inside of the eye being examined. In one example of the present invention, a 60-diopter lens manufactured by Volk Optical, with thickness of 13 mm and diameter of 31 mm is utilized as the objective lens 4.

The afore-mentioned linear polarizing filter 18 and the quarter-wave circular polarizing plate 20 as shown in FIG. 8 minimize internal reflections off the objective lens 4 from entering the image recorder 8. The combination of the linear polarizing filter 18 and quarter-wave plate 20 effectively blocks internal reflections from the front and back surface of objective lens. Light from the annular light source is unpolarized. Once it passes through the linear polarizer, the light becomes linearly polarized in a direction along the axis of the polarizer. When the linearly polarized light passes through the quarter wave plate, the light becomes circularly polarized. Upon reflection of the circularly polarized light from the surfaces of the objective lens, the light remains circularly polarized, but is rotating in the opposite direction. The reflected light will again pass through the circular polarizer and is converted to linearly polarized light. However, this linearly polarized light is rotated 90 degrees relative to the axis of the linear polarizer. The light is therefore blocked by the linear polarizer and cannot reach the image recorder. Light that is not reflected, but instead enters the eye and scatters from the retina is largely unpolarized and return through the quarter waveplate and linear polarizer to reach the image recorder.

In one preferred embodiment of the optical system 14 of the present invention, the space between the annular white-light emitter 12 and the linear polarizing filter 18 is minimized and preferably reduced to no separation so that internal reflections from the annular white-light emitter 12 off the linear polarizing filter 18 do not enter the digital camera.

In another preferred embodiment of the present invention, the combination of the coupling lens and the objective lens permits the annular white-light emitter to be imaged within the human pupil and an intermediate image of the retina is formed in the space between the coupling lens and the objective lens. This intermediate image can be visualized by the image recorder, as illustrated in FIG. 3. This is accomplished with an internal spacing of approximately 120 mm between the coupling lens and the objective lens and with an eye relief or distance from the eye to the objective lens of approximately 30 mm. The spacing between the coupling lens and the objective lens is chosen in combination with the focal length of the coupling lens. The coupling lens should match the size of the intermediate to the field of view of the image recorder and the coupling lens should re-image the intermediate image to a location where the image recorder can focus on it. The eye relief is chosen in combination with the focal length of the objective lens. The eye relief allows for patient comfort during fundus imaging, as well as controls the field of view of the retinal image.

In another preferred embodiment of the present invention, the annular light emitter 12 as described above includes a plurality of light-emitting diodes. In particular, white light-emitting diodes provide excellent color balance, and are very efficient in their conversion of electricity to light, so battery life is prolonged and large amounts of heat are not generated which could affect the eye. Further, the effective lifetime of the light-emitting diodes is extremely long, so provisions for changing of the light source and realignment of the illumination and imaging optics is not frequently required.

In the present embodiment of the invention, three LEDs are combined in series and gauged together in a group of four, for a total of 12 LEDs. This assembly is powered with a system of two 9-volt transistor radio batteries (H) and with a variable resistor to allow control of brightness (I), for a total current drain of 300 ma, which is within the current capacity of each of the individual light-emitting diodes.

Another concept is to utilize different color LEDs for different purposes, such as for example infrared IR and white light LEDs. In that case, alignment is performed with the infrared light, and the image is captured in white light. The pupil of the eye will dilate natural under darkened conditions. One desired use of the present invention is to capture images of the retina without the need to instill dilation drugs into the patient. Most digital cameras are sensitive to near-IR radiation. Using IR illumination in the camera allows the patient to be placed in a darkened environment where their pupils will naturally dilate. The eye examiner can visualize the patient's retina under IR illumination by observing the image (i.e., by watching the liquid crystal display LCD screen found on the back of the digital cameras). Once the patient's eye is aligned, the white LEDs are flashed on at the moment of image capture. The image of the internal structures of the eye will then be captured prior to the iris of the eye constricting in response to the white light.

Alternatively, white and green LEDs can be utilized to switch between white light and "red free" images. Furthermore, IR, Red, Green, Blue LEDs can be utilized. If red, green and blue are all on, the light source looks like a white light illumination, yet the IR LED can be used for patient alignment as discussed above, while the green LED can be used only for "red free" images.

Accordingly, in one preferred embodiment of the present invention, a phototransistor is utilized that can be exposed to a camera's flash. In this way, the camera's flash activates the phototransistor which through synchronizer 22, shown for example in FIG. 3, can turn the annular emitter 12 (i.e., turn on/off the LEDs) in synchronization with the flash of the digital camera. This permits utilization of conventional digital cameras without need for manufacture or user modifications. In this concept (i.e., a slave flash), the present inventors have determined that the fundus image can be captured during the time that the flash on the digital camera is fired. By adding the above noted phototransistor in sight of the flash for example on the optical mount as shown in FIG. 3, one can synchronize the annular light emitter 12 with the image capture of the image recorder 8 (i.e., the digital camera) without the need for modifications to the digital camera and/or additional wiring. With this approach, the present invention illuminates the retina of the patient with infrared light and aligns the patient using the LCD panel on the digital camera. Pressing the shutter starts the image capture and fires the digital camera flash. The phototransistor preferably included in the synchronizer 22 activates the synchronizer 22 which, in response to the digital camera flash, can turn on the white LEDs and off the IR LEDs off when the phototransistor is turned "on". The optical system 14 obscures the patient's eye from the flash, and therefore does not corrupt the image quality.

Figure 9:
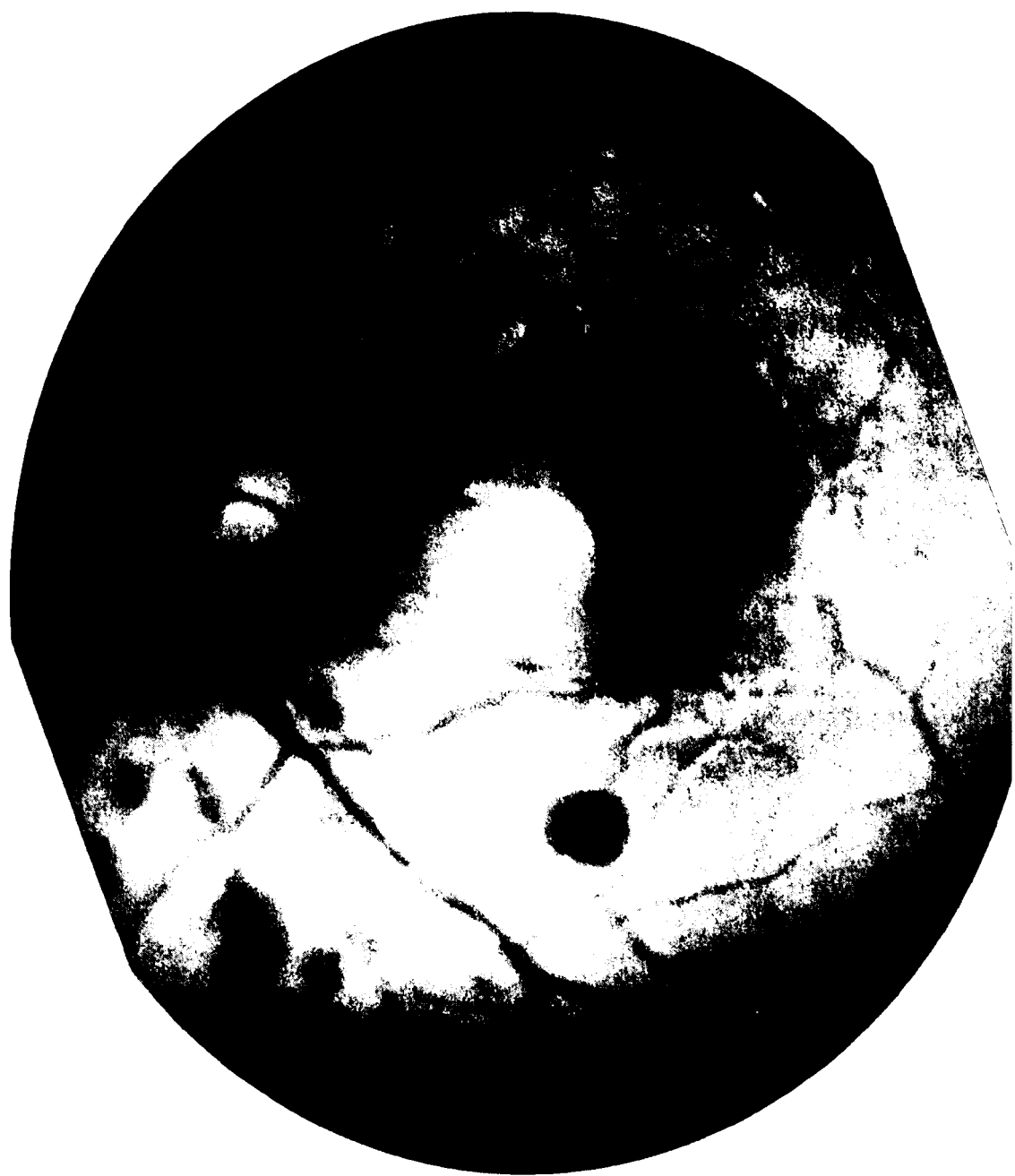
FIG. 9 is a photograph of a human ocular fundus taken according to the present invention.

Shown in FIG. 9 is an image taken by the imaging system of the present invention. In particular, FIG. 9 is an image of a human ocular fundus.

Figure 10:
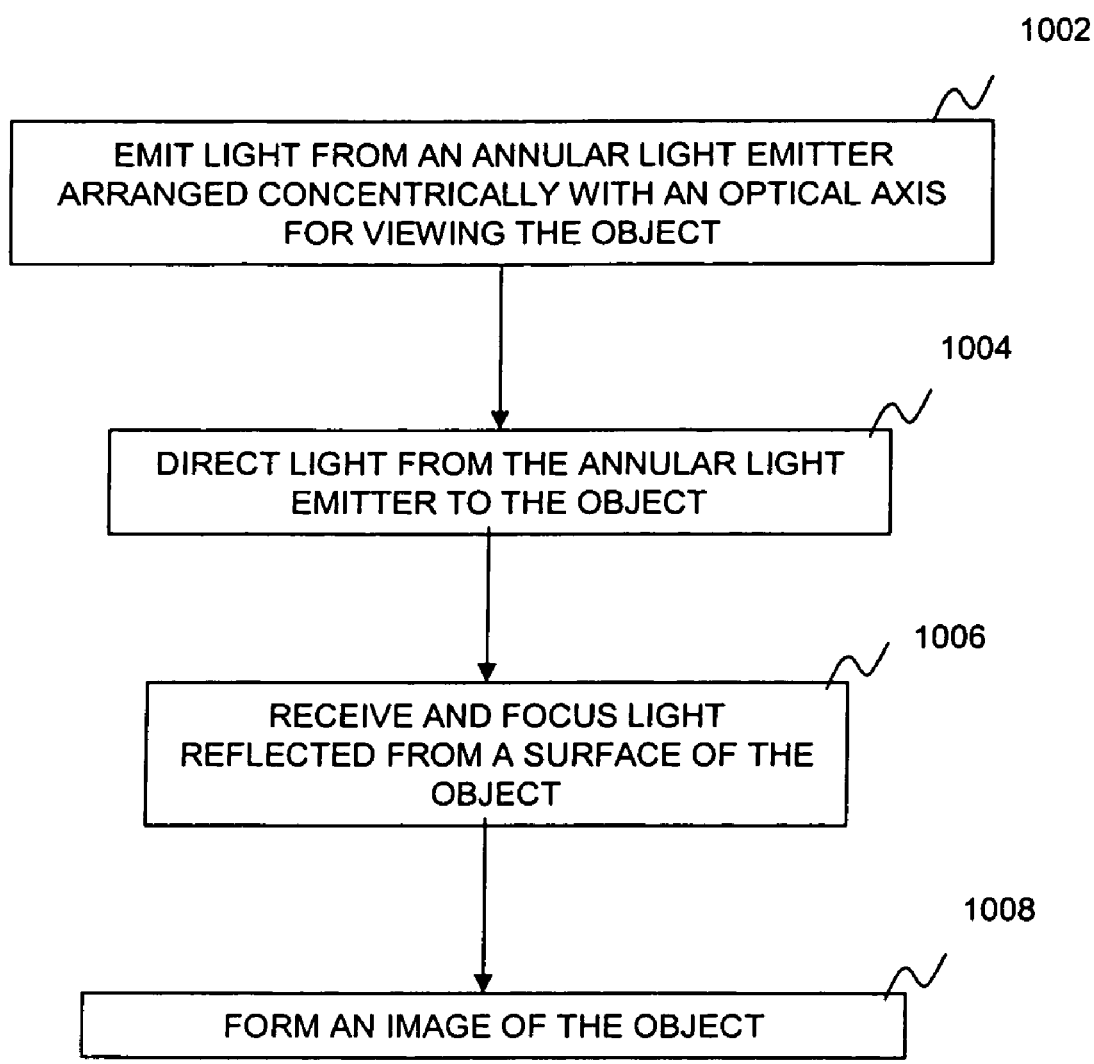
FIG. 10 is a flow chart illustrating the process of the present invention.

Hence, in general, the present invention includes systems and methods which can image any object, and therefore not limited to ocular fundus imaging. FIG. 10 is a flow chart illustrating the process of the present invention. As shown in FIG. 10, in step 1002, light is emitted from an annular light emitter arranged concentrically with an optical axis for illuminating the object. In step 1004, the light emitted from the annular light emitter is directed to the object. The annular light emitter is arranged concentrically with an optical axis for viewing the object. In step 1006, light reflected from a surface of the object is received and focused. In step 1008, an image of the object is formed.

The step 1002 preferably emits white light. The white light can be emitted from a white light emitting diode or a plurality of white light emitting diodes. The plurality of white light emitting diodes can be disposed on an annulus as shown in the figures. The white light can be generated by emitting red, green, and blue light, as from corresponding light emitting diodes. Additionally, an infrared light can be emitted to irradiate the object for alignment of the object prior to image capture.

In step 1004, the light directed to the object can be blocked such that light from the annular light emitter is not incident on a central region of an objective lens focusing the light into the interior of the object. Up to 10%, 50% and 90% of the light can be blocked from the central region of the objective lens. Further, in step 1004, the light directed to the object can be blocked such that light from the annular light emitter is not incident on a central region of a coupling lens receiving the reflected light from the objective lens. Up to 10%, 50% and 90% of the light can be blocked from the central region of the coupling lens.

In step 1006, the light reflected from the object can be focused at infinity and magnified to form the image of the object. Further, polarizing plates can be configured by respective polarizations of a linear polarizing filter and a quarter-wave circular polarizing plate to exclude from the image multiply reflected light.

In step 1008, an image of the object in the visible and infrared range can be formed. The image can be recorded in a digital camera. In one embodiment of the present invention, power to the annular light emitter can be synchronized upon a timed event such as for example a flash of a camera recording the image. Further, the image recorder of the present invention can record image streams of the object captured during observation of the object, and can store the image streams in a computer, such as for example computer 24 shown in FIG. 3. The computer 24 utilizes software to identify the best still image and/or to provide digital enhancements to the recorded images.

Figure 11:
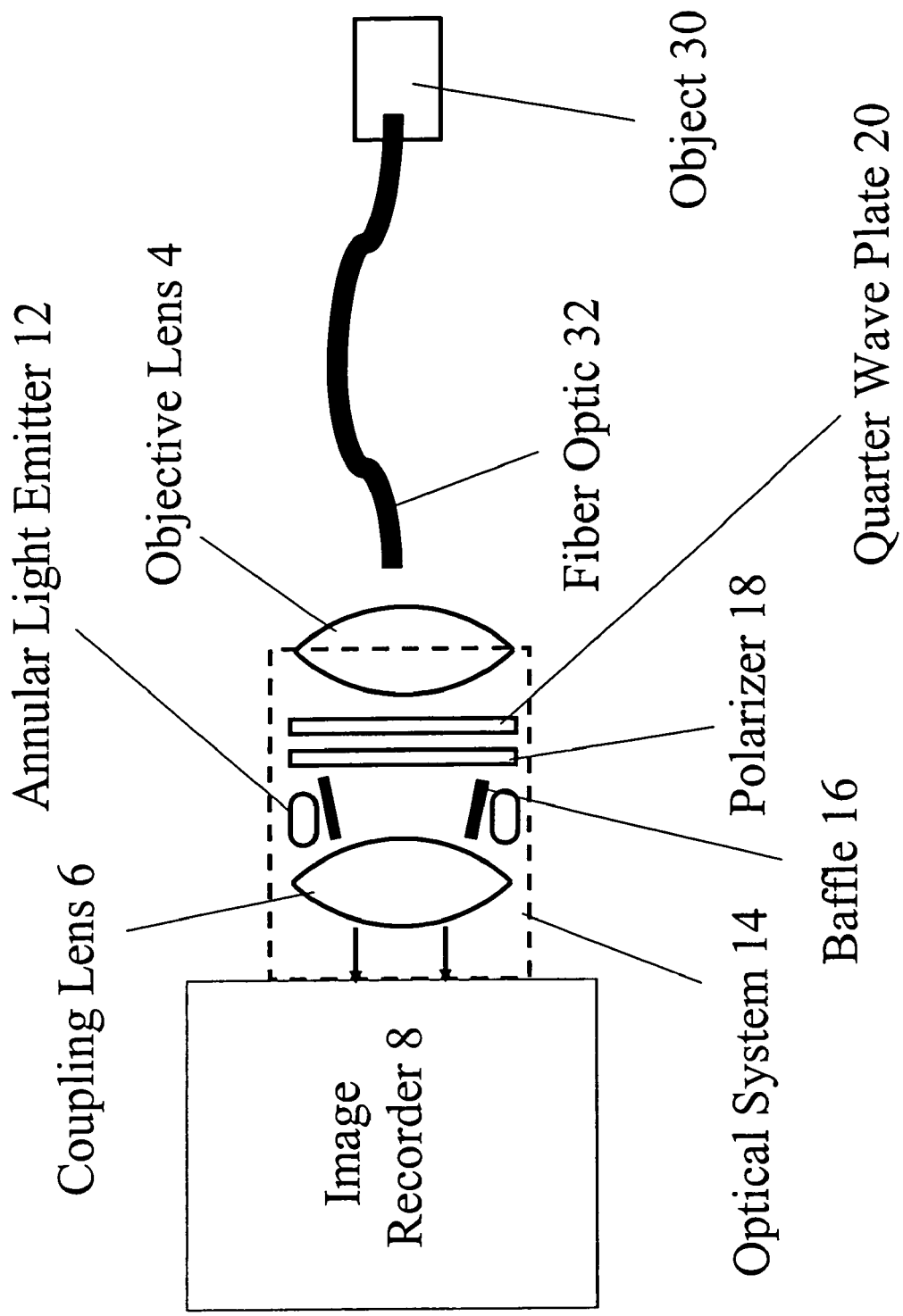
FIG. 11 is a schematic diagram of the novel imaging system of the present invention coupled to remote object for visualization of the object.

In one embodiment of the present invention, the interior of the object is imaged such as for example ocular fundus of an eye. As shown in FIG. 11, in another embodiment of the present invention, the image of the object 30 can be transmitted from a fiber optic 32 connecting the optical system 14 to the object 32. As such, the optical system of the present invention can be utilized for example by surgeons to examine joints in the human body or internal organs such as the heart or other vital organs, represented by the object 32 in FIG. 11. Thus, the optical system of the present invention can image various inanimate and animate objects. Accordingly, the optical system of the present invention can image the interior of objects such as machined or micromachined objects where inspection of the interior surfaces is normally difficult to image. Accordingly, the optical system of the present invention can image animate objects including both exterior and interior surfaces of organs such as the ocular fundus, internal organs such as for example the heart, stomach, or the intestines, joints such as for example the knee, and other internal body parts made accessible by insertion of a fiber optic. In that case, as know in the art, the objective lens would focus and match light to the aperture of the fiber optic. As before, these images can be captured as still frames as to a digital camera, or can be recorded as image streams in computer 24. The computer 24 as before can utilize software to identify the best still image and/or to provide digital enhancements to the recorded images.

Figure 12:
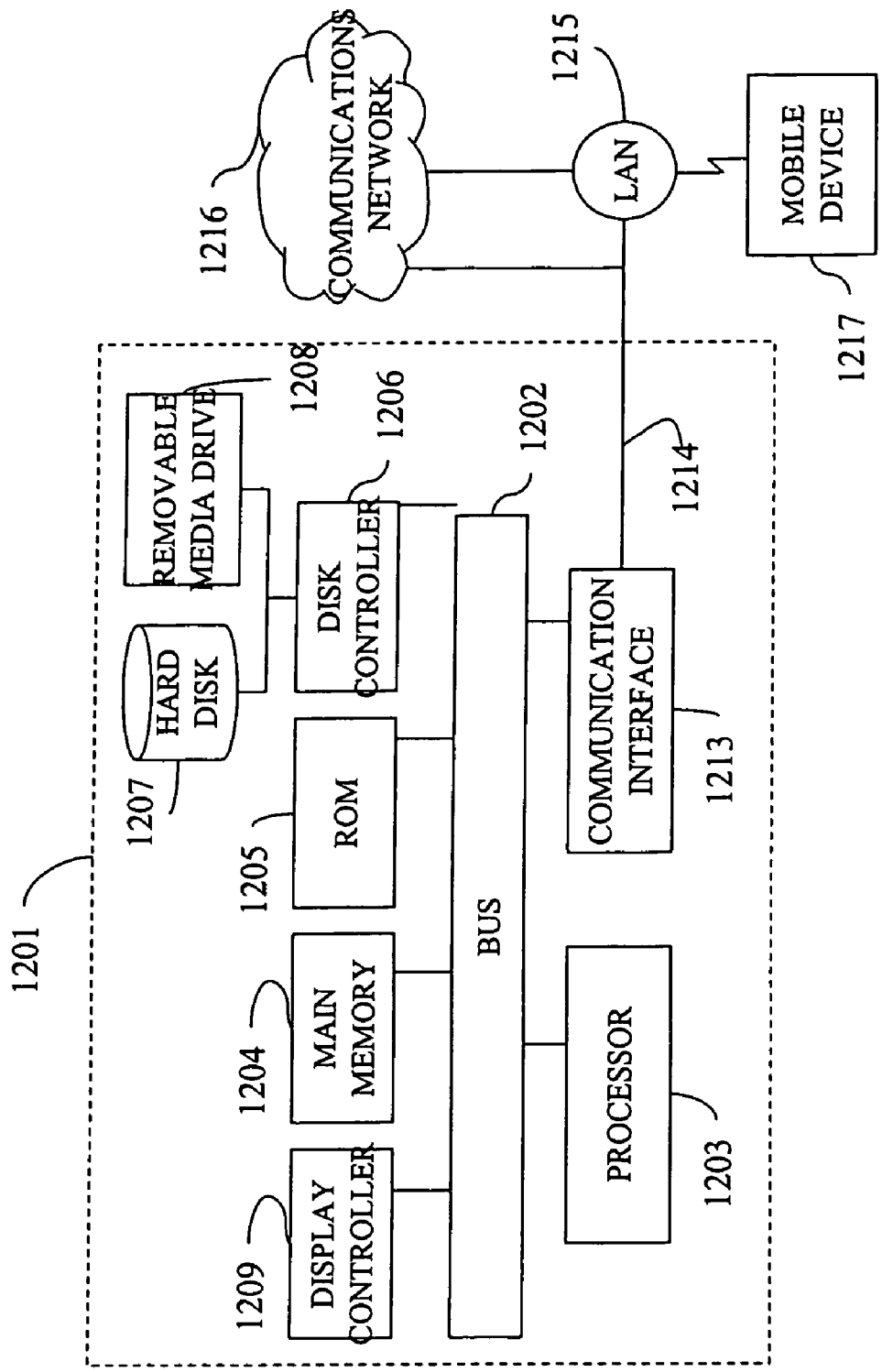
FIG. 12 illustrates a computer system for implementing various embodiments of the present invention.

Accordingly, FIG. 12 illustrates a computer system 1201 for implementing various embodiments of the present invention. The computer system 1201 may be used as the computer 24 to perform any or all of the functions of the computer 24 described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA). These storage devices can store the images of the objects or the image streams captured during observation of the object.

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to an observer such as for examiner a doctor or surgeon monitoring the images. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204.

In particular, the computer system 1201 can be programmed to image an object by performing the steps of controlling light emission from an annular light emitter arranged concentrically with an optical axis for illuminating the object, and capturing the image of the object from light directed to the object from the annular light emitter, reflected from a surface of the object, and imaged onto an image recorder. Further, the computer system 1201 can be programmed to perform the step of synchronizing power to the annular light emitter upon a timed event, and thereafter recording the image of the object upon a flash of a camera. The computer system 1201 can be programmed to perform the step of capturing image streams of the object, and thereafter selecting still images from the image streams.

Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

Numerous modifications and variations of the present invention are possible in light of the above teachings. It is therefore to be understood that within the scope of the appended claims, the invention may be practiced otherwise than as specifically described herein.

The invention claimed is:

1. A system for imaging an object of an organ, comprising:
    an objective lens configured to direct light to the object;
    a coupling lens configured to receive light reflected from a surface of the object and transmitted through the objective lens, and to focus the reflected light as an image of the object;
    an annular light emitter arranged concentrically with an optical axis of the objective lens and the coupling lens, and configured to emit to the objective lens the light directed to the object; and
    a baffle inserted in an optical path from the annular light emitter and the objective lens, and having a taper whose elongated portion is configured to block a part of the emitted light from the annular light emitter from being incident on a central region of the objective lens.

2. The system of claim 1, wherein the annular light emitter comprises:
    a white light emitter.

3. The system of claim 2, wherein the white light emitter comprises:
    a white light emitting diode.

4. The system of claim 3, wherein the white light emitting diode comprises:
    a plurality of white light emitting diodes; and
    a ring support configured to position said plurality of said white light emitting diodes off axis from a central axis extending from the coupling lens to the objective lens.

5. The system of claim 2, wherein the white light emitter comprises:
    a red light emitting diode;
    a green light emitting diode; and
    a blue light emitting diode.

6. The system of claim 5, further comprising:
    an infrared light emitting diode configured to irradiate the object with infrared light for alignment of the object prior to image capture.

7. The system of claim 6, further comprising:
    an image recorder configured to capture the image of the object in an infrared range.

8. The system of claim 1, wherein the annular light emitter comprises:
    a plurality of light emitting diodes including at least one of a red light emitting diode, a green light emitting diode, and a blue light emitting diode.

9. The system of claim 8, further comprising:
    an infrared light emitting diode configured to irradiate the object with infrared light for alignment of the object prior to image capture.

10. The system of claim 9, further comprising:
    an image recorder configured to capture the image of the object in an infrared range.

11. The system of claim 10, wherein the image recorder is configured to capture the image of the object in a visible range.

12. The system of claim 1, wherein the coupling lens is configured to be focused at infinity and is configured to magnify the image of the object.

13. The system of claim 12, wherein the coupling lens comprises:
    a refractive lens having a range of refractive power from 5 to 60 diopter.

14. The system of claim 13, wherein the coupling lens has a refractive power of at least 10 diopter.

15. The system of claim 1, wherein the objective lens comprises:
    a refractive lens having a range of refractive power from 20 to 90 diopter.

16. The system of claim 15, wherein the objective lens has a refractive power of at least 60 diopter.

17. The system of claim 1, further comprising:
    a support for the annular light emitter, the objective lens, and the coupling lens.

18. The system of claim 17, further comprising:
an image recorder connected to the support and configured to capture the image.

19. The system of claim 18, wherein the image recorder comprises a digital camera.

20. The system of claim 1, further comprising:
an image recorder configured to capture the image.

21. The system of claim 20, wherein the image recorder comprises a camera.

22. The system of claim 21, further comprising:
a computer;
said camera configured to record image streams; and
said computer configured to produce still images from the image streams.

23. The system of claim 1, further comprising:
an image recorder configured to capture the image and record image streams; and
a computer configured to produce still images from the image streams.

24. The system of claim 1, wherein the annular light emitter and the baffle are positioned between the coupling lens and the objective lens.

25. The system of claim 24, wherein the baffle is disposed concentric to the optical axis and interior to the annular light emitter, and extends radially to block a part of the emitted light that would be incident on a central region of the objective lens.

26. The system of claim 25, wherein the baffle comprises:
a conical frustum.

27. The system of claim 25, wherein the baffle is configured to block at least 10% of the objective lens from receiving said emitted light.

28. The system of claim 25, wherein the baffle is configured to block at least 50% of the objective lens from receiving said emitted light.

29. The system of claim 25, wherein the baffle is configured to block at least 90% of the objective lens from receiving said emitted light.

30. The system of claim 1, wherein the annular light emitter and the baffle are positioned between the image recorder and the coupling lens.

31. The system of claim 30, wherein the baffle is disposed concentric and interior to the annular light emitter, and extends radially to block a part of the emitted light that would be incident on a central region of the objective lens and the coupling lens.

32. The system of claim 31, wherein the baffle comprises:
a conical frustum.

33. The system of claim 31, wherein the baffle is configured to block at least 10% of the objective lens from receiving said emitted light.

34. The system of claim 31, wherein the baffle is configured to block at least 10% of the coupling lens from receiving said emitted light.

35. The system of claim 31, wherein the baffle is configured to block at least 50% of the objective lens from receiving said emitted light.

36. The system of claim 31, wherein the baffle is configured to block at least 50% of the coupling lens from receiving said emitted light.

37. The system of claim 31, wherein the baffle is configured to block at least 90% of the objective lens from receiving said emitted light.

38. The system of claim 31, wherein the baffle is configured to block at least 90% of the coupling lens from receiving said emitted light.

39. The system of claim 1, further comprising:
a linear polarizing filter and a quarter-wave circular polarizing plate disposed between the coupling lens and the objective lens.

40. The system of claim 31, wherein the linear polarizing filter and the quarter-wave circular polarizing plate are configured by respective polarizations of the linear polarizing filter and the quarter-wave circular polarizing plate to exclude from said image multiply reflected light.

41. The system of claim 1, wherein the coupling lens and the objective lens are separated by a distance from 80–150 nm.

42. The system of claim 1, further comprising:
a synchronizer configured to power the annular light emitter upon a timed event.

43. The system of claim 42, further comprising:
a camera configured to record the image of the object; and
said synchronizer is configured to power the annular light emitter upon a flash of a camera.

44. The system of claim 1, wherein the objective lens is configured to image an interior of the object.

45. The system of claim 44, wherein the objective lens is configured to image an ocular fundus.

46. The system of claim 1, further comprising:
a fiber optic connected between the objective lens and the object.

47. The system of claim 46, wherein the objective lens is configured to image an interior of the object.

48. The system of claim 47, wherein the objective lens is configured to image at least one of an organ, an internal organ, a joint, and an internal body part.

49. A system for imaging an object of an organ, comprising:
a light source configured to emit light for illumination of the object;
an objective lens configured to direct said light to the object;
a coupling lens configured to receive light reflected from a surface of the object and transmitted through the objective lens, and to focus the received light as an image of the object;
a baffle inserted in an optical path from the light source and the objective lens, and having a taper whose elongated portion is configured to block a part of the emitted light from the light source from being incident on the objective lens; and
said baffle configured to block light from the light source from being incident on a central region of the objective lens.

50. A system for imaging an object of an organ, comprising:
a light source configured to emit light for illumination of the object;
an objective lens configured to direct said light to the object;
a coupling lens configured to receive light reflected from a surface of the object and transmitted through the objective lens, and to focus the received light as an image of the object;
a baffle inserted in an optical path from the light source and the objective lens, and having a taper whose elongated portion is configured to block a part of the emitted light from the light source from being incident on a central region of the objective lens; and
said light source including an infrared light source configured to irradiate the object with infrared light for alignment of the object prior to image capture.

51. A system for imaging an object of an organ, comprising:
- a light source configured to emit light for illumination of the object;
- an objective lens configured to direct said light to the object;
- a coupling lens configured to receive light reflected from a surface of the object and transmitted through the objective lens, and to focus the received light as an image of the object;
- a baffle inserted in an optical path from the light source and the objective lens, and having a taper whose elongated portion is configured to block a part of the emitted light from the light source from being incident on the objective lens; and
- said light source including a white light emitting diode and a green light emitting diode.

52. A method for imaging an object of an organ, comprising:
- emitting light from an annular light emitter arranged concentrically with an optical axis for illuminating the object;
- directing said light to the object with a part of the emitted light being blocked by an elongated portion of a tapered baffle inserted in an optical path from the annular light emitter and an objective lens for imaging the object, said baffle being configured to block light from the annular light emitter from being incident on a central region of the objective lens;
- receiving and focusing reflected light from a surface of the object; and
- forming an image of the object.

53. The method of claim 52, wherein the emitting visible light comprises:
- emitting white light.

54. The method of claim 53, wherein the emitting white light comprises:
- emitting white light from a white light emitting diode.

55. The method of claim 54, wherein the emitting white light from a white light emitting diode comprises:
- emitting white light from a plurality of white light emitting diodes disposed on an annulus.

56. The method of claim 53, wherein the emitting white light comprises:
- emitting red, green, and blue light.

57. The method of claim 56, wherein the emitting red, green, and blue light comprises:
- emitting light from a red light emitting diode,
- emitting light from a green light emitting diode, and
- emitting light from a blue light emitting diode.

58. The method of claim 52, further comprising:
- capturing the image of the object in a visible range.

59. The method of claim 52, wherein the emitting comprises:
- emitting an infrared light to irradiate the object for alignment of the object prior to image capture.

60. The method of claim 59, further comprising:
- capturing the image of the object in an infrared range.

61. The method of claim 52, wherein the receiving and focusing light reflected from an interior surface of the object comprises:
- focusing the reflected light at infinity; and
- magnifying the image of the object.

62. The method of claim 52, wherein the forming an image of the object comprises:
- forming an image in a camera.

63. The method of claim 52, wherein the forming an image of the object comprises:
- forming image streams of the object.

64. The method of claim 52, wherein the forming image streams further comprises:
- selected still images from the image streams.

65. The method of claim 52, wherein the directing said light into the interior of the object comprises:
- blocking light from the annular light emitter from being incident on a central region of an objective lens focusing the light from the annular light emitter into the interior of the object.

66. The method of claim 65, wherein the blocking light comprises:
- excluding at least 10% of the objective lens from receiving the light.

67. The method of claim 65, wherein the blocking light comprises:
- excluding at least 50% of the objective lens from receiving the light.

68. The method of claim 65, wherein the blocking light comprises:
- excluding at least 90% of the objective lens from receiving the light.

69. The method of claim 52, wherein the directing said light into the interior of the object comprises:
- blocking light from the annular light emitter from being incident on a central region of a coupling lens receiving said reflected light from the interior of the object.

70. The method of claim 69, wherein the blocking light comprises:
- excluding at least 10% of the coupling lens from receiving the light.

71. The method of claim 69, wherein the blocking light comprises:
- excluding at least 50% of the coupling lens from receiving the light.

72. The method of claim 69, wherein the blocking light comprises:
- excluding at least 90% of the coupling lens from receiving the light.

73. The method of claim 52, the forming an image of the object comprises:
- utilizing polarizing plates to exclude from said image multiply reflected light.

74. The method of claim 52, further comprising:
- synchronizing power to the annular light emitter upon a timed event.

75. The method of claim 74, further comprising:
- recording the image of the object upon a flash of a camera.

* * * * *